United States Patent
Kaline

(10) Patent No.: US 10,617,634 B1
(45) Date of Patent: Apr. 14, 2020

(54) TOPICAL HOMEOPATHIC FORMULATIONS FOR MENSTRUAL CRAMPS

(71) Applicant: Biolyte Laboratories, LLC, Grand Rapids, MI (US)

(72) Inventor: Daniel Kaline, Wyoming, MI (US)

(73) Assignee: Biolyte Laboratories, LLC, Grand Rapids, MI (US)

(*) Notice: Subject to any disclaimer, the term of this patent is extended or adjusted under 35 U.S.C. 154(b) by 46 days.

(21) Appl. No.: 15/910,622

(22) Filed: Mar. 2, 2018

Related U.S. Application Data

(60) Provisional application No. 62/470,083, filed on Mar. 10, 2017.

(51) Int. Cl.
| | | |
|---|---|---|
| A61K 36/00 | (2006.01) | |
| A61K 9/00 | (2006.01) | |
| A61K 36/14 | (2006.01) | |
| A61K 35/64 | (2015.01) | |
| A61K 47/32 | (2006.01) | |
| A61K 47/02 | (2006.01) | |
| A61K 47/12 | (2006.01) | |
| A61K 47/10 | (2017.01) | |
| A61K 36/28 | (2006.01) | |
| A61K 36/81 | (2006.01) | |
| A61K 36/287 | (2006.01) | |
| A61K 36/42 | (2006.01) | |
| A61K 36/33 | (2006.01) | |
| A61K 36/29 | (2006.01) | |
| A61K 36/71 | (2006.01) | |
| A61K 36/185 | (2006.01) | |
| A61K 36/48 | (2006.01) | |
| A61K 36/8967 | (2006.01) | |
| A61K 36/72 | (2006.01) | |
| A61K 9/06 | (2006.01) | |

(52) U.S. Cl.
CPC ............ *A61K 9/0014* (2013.01); *A61K 9/06* (2013.01); *A61K 35/64* (2013.01); *A61K 36/14* (2013.01); *A61K 36/185* (2013.01); *A61K 36/28* (2013.01); *A61K 36/287* (2013.01); *A61K 36/29* (2013.01); *A61K 36/33* (2013.01); *A61K 36/42* (2013.01); *A61K 36/48* (2013.01); *A61K 36/71* (2013.01); *A61K 36/72* (2013.01); *A61K 36/81* (2013.01); *A61K 36/8967* (2013.01); *A61K 47/02* (2013.01); *A61K 47/10* (2013.01); *A61K 47/12* (2013.01); *A61K 47/32* (2013.01)

(58) Field of Classification Search
None
See application file for complete search history.

(56) References Cited

U.S. PATENT DOCUMENTS

| | | |
|---|---|---|
| 5,006,338 A | 4/1991 | Luenemann |
| 5,997,876 A | 12/1999 | Shikhashvili et al. |
| 6,146,639 A | 11/2000 | Merich |
| 6,447,788 B1 | 9/2002 | Strathausen |
| 6,770,263 B1 | 8/2004 | Brucker |
| 7,229,648 B2 | 6/2007 | Dreyer |
| 7,351,739 B2 | 4/2008 | Ho et al. |
| 7,781,429 B2 | 8/2010 | Schwarz et al. |
| 7,871,647 B1 | 1/2011 | Paradise |
| 9,545,429 B1 * | 1/2017 | Kaline ............... A61K 36/00 |
| 2006/0165812 A1 * | 7/2006 | Charron ............. A61K 33/00 424/600 |
| 2007/0134299 A1 | 6/2007 | Giles |
| 2007/0212434 A1 * | 9/2007 | Day ..................... A61K 8/498 424/762 |
| 2008/0038219 A1 | 2/2008 | Mosbaugh et al. |
| 2008/0145454 A1 | 6/2008 | Wycoff |
| 2009/0232904 A1 | 9/2009 | Quinto et al. |
| 2010/0316737 A1 | 12/2010 | Farrington et al. |
| 2011/0038949 A1 | 2/2011 | Oswal et al. |

FOREIGN PATENT DOCUMENTS

| | | |
|---|---|---|
| DE | 3316726 | 11/1984 |
| FR | 2255887 | 7/1975 |
| GB | 2311009 | 9/1997 |
| RU | 2190419 | 10/2002 |

OTHER PUBLICATIONS

Berrebi et al., Treatment of pain due to unwanted lactation with a homeopathic preparation given in the immediate post-partum period, 30 J Gynecol Obstet Biol Reprod (Paris) 353-57 (2001) (English Abstract Provided).

(Continued)

*Primary Examiner* — Ralph J Gitomer
(74) *Attorney, Agent, or Firm* — Adam R. Stephenson, Ltd.

(57) ABSTRACT

Implementations of a topical homeopathic formulation may include an active portion including a plurality of active ingredients and a base including a plurality of inactive ingredients. The plurality of active ingredients may include one of tinctures and homeopathic preparations of *Apis mellifica, Arnica montana, Atropa belladonna, Bellis perennis, Bryonia alba, Cactus grandifloras, Caulophyllum thalictroides, Cimicifuga racemose, Citrullus colocynthis, Cyclamen europaeum, Gelsemium Sempervirens, Gnaphalium polycephalum, Jonesia asoca, Juniperus Sabina, Kali carbonicum, Lilium tigrinum, Rhamnus californica, Tilia europaea, Viburnum opulus*, and any combination thereof.

18 Claims, No Drawings

(56) References Cited

OTHER PUBLICATIONS

Canadian Intellectual Property Office, dated Nov. 4, 2011 Search Report for App. No. 2518965.
Cordova et al., Protective properties of butanolic extract of the *Calendula officinalis* L. (marigold) against lipid peroxidation of rat liver microsomes and action as free radical scavenger, 7 Redox Rep 95-102 (2002).
Dr. Frank's Joint & Muscle Pain Relief product information, retrieved from https://www.drfrankspainrelief.com/formula.php on Aug. 19, 2011.
USPTO, Jun. 9, 2005 Examiner-Initiated Interview Summary for U.S. Appl. No. 10/797,009.
GMI's PainMed product information, retrieved from http://gmipainmed.com/PAIN_MED_ACTIVE_INGREDIENTS.html on Aug. 19, 2011.
USPTO, Sep. 24, 2004 PCT International Search Report for PCT/US04/05231.
Epicure product label. Available at least as early as 2016.
Friese et al., The homeopathic treatment of otitis media in children—comparisons with conventional therapy, 35 International Journal of Clinical Pharmacology and Therapeutics 296-301 (1997) (last page missing).
HomeopathyHome.com web pages, retrieved through web.archive.org website. Available at least as early as 2001.
911 Stress Control product information website, retrieved through web.archive.org website. Available at least as early as Feb. 23, 2002.
USPTO, Jun. 21, 2005 Office Action (Non-Final Rejection) of U.S. Appl. No. 10/797,009.
Knuesel et al., Arnica montana gel in osteoarthritis of the knee: an open, multicenter clinical trial, 19 Adv Ther 209-18 (2002).
Kumar et al, Anti-inflammatory and analgesic activity of Indian *Hypericum perforatum* L., 39 Indian J Exp Biol 339-43 (2001).
Painazol product information, retrieved from http://www.painazol.com/?ssid=0e1d611447ad692e7c278fc08a2026b0 on Aug. 19, 2011.
Rhumatol product information, retrieved from http://www.rhumatol.com/?ssid=0e1d611447ad692e7c278fc08a2026b0 on Aug. 19, 2011.
Traumeel product label. Available at least as early as 2016.
van Haselen et al., A randomized controlled trial comparing topical piroxicam gel with a homeopathic gel in osteoarthritis of the knee, 39 Rheumatology 714-19 (2000).
Painazol Pain Relief Marketing Information (marketing start date: May 20, 2010).
Trace Mineral Reviews, available at www.trace-mineral-drops.com. Available at least as early as Jan. 6, 2014.

\* cited by examiner

TOPICAL HOMEOPATHIC FORMULATIONS FOR MENSTRUAL CRAMPS

CROSS REFERENCE TO RELATED APPLICATIONS

This document claims the benefit of the filing date of U.S. Provisional Patent Application 62/470,083, entitled "Menstrual Cramp Homeopathic Formulation and Related Methods" to Dan Kaline which was filed on Mar. 3, 2017, the disclosure of which is hereby incorporated entirely herein by reference.

BACKGROUND

Technical Field

Aspects of this document relate generally to homeopathic compositions used for treating pain and cramping symptoms. More specific implementations involve compositions used for treating menstrual cramps and/or pain in the ovaries.

2. Background

A large number of plant and animal extracts and chemicals have been observed to, in diluted quantities, enable healing and reduction of symptoms associated with diseases and injuries of the (human or animal) body. Homeopathic compositions operate using diluted concentrations of substances that modify the frequency of the diluent and have been observed to produce a corresponding response within the body when applied externally or taken internally.

SUMMARY

Implementations of a topical homeopathic formulation may include an active portion including a plurality of active ingredients and a base including a plurality of inactive ingredients. The plurality of active ingredients may include one of tinctures and homeopathic preparations of *Apis mellifica, Arnica montana, Atropa belladonna, Bellis perennis, Bryonia alba, Cactus grandifloras, Caulophyllum thalictroides, Cimicifuga racemose, Citrullus colocynthis, Cyclamen europaeum, Gelsemium Sempervirens, Gnaphalium polycephalum, Jonesia asoca, Juniperus Sabina, Kali carbonicum, Lilium tigrinum, Rhamnus californica, Tilia europaea, Viburnum opulus*, and any combination thereof.

Implementations of topical homeopathic compositions may include one, all, or any of the following:

The base may include acrylates/C-10-30 alkyl acrylate cross-polymer, colloidal silver, potassium sorbate, citric acid, fulvic acid, water, sodium hydroxide, vegetable glycerin, and any combination thereof.

The base may be a gel base and includes acrylates/C-10-30 alkyl acrylate cross-polymer, vegetable glycerin, colloidal silver, citric acid, fulvic liquid minerals, potassium sorbate, water, and sodium hydroxide.

The fulvic liquid mineral composition may include 73 trace minerals.

The actives portion may include 50% to 90% by weight of the total formulation and the inactives portion may include 10%-50% by weight of the total formulation.

The base may include an 18% sodium hydroxide solution.

The base may include ethanol.

Implementations of a topical homeopathic formulation may include an active portion including a plurality of active ingredients and a base including a plurality of inactive ingredients. The plurality of active ingredients may include one of tinctures and homeopathic preparations of *Apis mellifica, Arnica montana, Atropa belladonna, Bellis perennis, Bryonia alba, Cactus grandifloras, Caulophyllum thalictroides, Cimicifuga racemose, Citrullus colocynthis, Cyclamen europaeum, Gelsemium Sempervirens, Gnaphalium polycephalum, Jonesia asoca, Juniperus Sabina, Kali carbonicum, Lilium tigrinum, Rhamnus californica, Tilia europaea, Viburnum opulus*, and any combination thereof. The base may include one of acrylates/C-10-30 alkyl acrylate cross-polymer, vegetable glycerin, colloidal silver, citric acid, fulvic liquid minerals, potassium sorbate, water, and sodium hydroxide.

Implementations of topical homeopathic compositions may include one, all, or any of the following:

The base may include one of acrylates/C-10-30 alkyl acrylate cross-polymer, colloidal silver, potassium sorbate, citric acid, fulvic acid, water, sodium hydroxide, vegetable glycerin, and any combination thereof.

The fulvic liquid mineral composition may include 73 trace minerals.

The actives portion may include 50% to 90% by weight of the total formulation and the inactives portion may include 10%-50% by weight of the total formulation.

The base may include an 18% sodium hydroxide solution.

The base may include ethanol.

Implementations of a topical homeopathic formulation may include an active portion including a plurality of active ingredients and a base including a plurality of inactive ingredients. The plurality of active ingredients may include one of tinctures and homeopathic preparations of *Apis mellifica, Arnica montana, Atropa belladonna, Bellis perennis, Bryonia alba, Cactus grandifloras, Caulophyllum thalictroides, Cimicifuga racemose, Citrullus colocynthis, Cyclamen europaeum, Gelsemium Sempervirens, Gnaphalium polycephalum, Jonesia asoca, Juniperus Sabina, Kali carbonicum, Lilium tigrinum, Rhamnus californica, Tilia europaea, Viburnum opulus*, and any combination thereof. The base may include acrylates/C-10-30 alkyl acrylate cross-polymer, vegetable glycerin, colloidal silver, citric acid, fulvic liquid minerals, potassium sorbate, water, and sodium hydroxide.

Implementations of topical homeopathic compositions may include one, all, or any of the following:

The fulvic liquid mineral composition may include 73 trace minerals.

The actives portion may include 50% to 90% by weight of the total formulation and the inactives portion may include 10%-50% by weight of the total formulation.

The base may include an 18% sodium hydroxide solution.

The base may include ethanol.

The foregoing and other aspects, features, and advantages will be apparent to those artisans of ordinary skill in the art from the DESCRIPTION and DRAWINGS, and from the CLAIMS.

DESCRIPTION

This disclosure, its aspects and implementations, are not limited to the specific components, assembly procedures or method elements disclosed herein. Many additional components, assembly procedures and/or method elements known in the art consistent with the intended homeopathic formulations will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such homeopathic formulations, and implementing components and methods, consistent with the intended operation and methods.

Dr. Samuel Hahnemann (1755-1843), a German physician considered by many to be the father of Homeopathy, believed that human beings have a capacity for healing themselves and that the symptoms of disease reflect the individual's struggle to overcome their illness. He discovered the principle that, what a particular substance could cause in the way of symptoms, that substance could also cure. Based on this understanding, Hahnemann proposed the "Law of Similars" In other words, if someone has certain symptoms, then regardless of the disease involved, taking a medicine that causing the same symptoms but highly diluted would produce opposite symptoms. In homeopathic medicine, this later became known as the "law of Infinitesimals." Homeopathic medicines and substances are considered by homeopaths to act as remedies by creating Informational Energy, stimulating the internal vital force of the body, and thereby initiating an immune and healing response within the body to heal itself. In practice, while little or no side adverse side effects may be observed because of the dilution, a strong positive effect can be seen as the sub-atomic frequency of the solution works with the body.

Homeopathy operates on a different principle than conventional over-the-counter pharmaceutical preparations. In conventional pharmaceutical preparations, those solutions that are most concentrated in a particular component are considered least potent, while those that are least concentrated (highly diluted) in a particular component are most potent. Based on the general principle of treating like with like, homeopathic preparations work using components that in large doses would create symptoms like those the patient is currently experiencing. However, by deliberately applying sequentially highly diluted or "potentized" preparations of these same components through a process called "succussion," the patient's body can be stimulated to take the actions needed to eliminate the symptoms associated with the disease and help facilitate the healing needed to recover from an injury. This means that in homeopathic compositions, a more diluted preparation is more potentized, and therefore, is designed to produce a stronger effect on the body (in contrast with the approach of conventional pharmaceutical compositions). Each component of a homeopathic mixture is made from a plant, chemical compound, or animal in the form of a tincture at a specified concentration or ratio of ethyl alcohol. The tincture is then sequentially diluted or succussed to a desired dilution to form a homeopathic preparation. Homeopathic ingredients that have been highly diluted are also referred to as high potency. Ultra high dilutions that may be used can produce solutions in which it may be close to physically impossible for a single molecule from the original component to be present in the solution applied. Homeopaths may refer to the process of succussing a tincture as establishing the frequency of the solution and using the resulting frequency of the solution to work with the body to provoke/promote a healing response.

Several different dilution scales are used in homeopathy to describe the end concentration of a given homeopathic preparation for a particular component. The centesimal or C scale is based on diluting by a factor of 100 at each stage. For example, to create a 1C solution, 99 drops of diluent would be added to 1 drop of a tincture of the component. To create a 2C solution, 99 drops of diluent would be added to 1 drop of a 1C solution of the component. The decimal or D scale is based on diluting by a factor of 10 at each stage, or by adding 9 drops of diluent to 1 drop of tincture to create a 1× or 1D solution. A 100× solution would be created by starting with a 1× solution and then repeating the process of taking one drop of the last dilution and adding 9 more drops of diluents to it 9 additional times. This type of dilution is base 10 logarithmic in scale. The quintamillesimal (Q) or LM scale is the process of creating a dilution of 1:50,000 in the first dilution. Accordingly, an LM-1 homeopathic preparation is prepared by sequentially succussing one drop of tincture with 49,999 drops of diluent. In practice, homeopathic preparations of given components range in dilution from tincture to 400× on the Decimal scale, tincture to 200 C on the C scale, and LM-1 to LM-3 on the LM scale.

The observed effectiveness of a given homeopathic preparation can depend upon the method used to administer it to the patient. For example, lower potency (higher concentration) homeopathic ingredients appear to have better results when used as a topical treatment application when compared to high potency ingredients. In contrast, high potency homeopathic ingredients work well when administered orally or internally. A potential problem with administering lower potency homeopathic preparations such as tinctures, 1×, 2×, 3× and 4× dilutions topically is that homeopathic ingredients are cut with ethyl alcohol as a preservative during the preparation process and also to produce the mother tinctures for further dilution to increase potency. As a result, tinctures and 1× potencies can contain between about 30 to about 60% ethyl alcohol. This high concentration of ethanol may be necessary to prevent bacterial growth while still retaining the benefit of the active ingredient. However, this higher concentration of ethyl alcohol may in itself be less than idea to apply to the skin or ingest orally by the patient. Low potency ingredients may work well when the benefit of the ingredient is not necessarily being used in the homeopathic capacity of like curing like, but is being used like a conventional pharmaceutical preparation. However, if a homeopathic ingredient is used in lower potency where the application of the homeopathic ingredient is intended to operate homeopathically based on the principle of like curing like, then low potency application of those ingredients could pose a potential health risk to the skin itself due to the high concentration of the particular component in what is being applied to the skin.

Low potency ingredients may also present challenges when compared to high potency mixtures in that they tend to be less stable over time and characteristically have a much shorter shelf life. High potency ingredients, due to the very low concentration of ethanol and/or high amount of purified water diluent, tend to perform better in terms of stability and longer shelf life. Another challenge, from the homeopath's perspective, with low potency homeopathic preparations is that although they may perform well topically, they may also lack the ability to affect tissues deeper in the body. When a solution is prepared for the purpose of homeopathic topical application, a strategy is to blend in both low and high potency ingredients together (i.e., include both a 1× preparation and a 20× preparation of the same component in the same product) to provide a dual benefit. This may not be as safe when strictly using higher potency ingredients when the solution is to be administered to younger people who will be more sensitive to the effects of the lower potency ingredients (unless the monograph calls for tincture external use, where low dilutions can provide a benefit for a particular ingredient). Such specifically monographed ingredients for use at tincture external use can provide a benefit for both low and high dilutions.

The various components included in implementations of homeopathic preparations disclosed in this document are selected from those officially listed in the Homeopathic Pharmacopoeia of the United States (HPUS). A description of the specific symptoms each of the components disclosed in this document that may work to remedy the particular conditions disclosed herein may be found in William Boericke, M. D., *Materia Medica,* 9th Edition (1927), the disclosures of which for each components disclosed in this document is hereby incorporated herein by reference.

Various implementations of homeopathic compositions and implementations of methods of using the same are disclosed in this document. In this document, the various implementations may be useful for treating human women's menstrual cramps and/or pain from the ovaries induced during ovulation or menstruation. The homeopathic formulas disclosed herein may also be used to relieve other pain or discomfort, including other cramps.

Implementations of topical homeopathic compositions disclosed in this document may include an actives portion including a plurality of active ingredients and a base including a plurality of inactive ingredients. The plurality of active ingredients may include tinctures and/or homeopathic preparations of *Apis mellifica* (Honey Bee), *Arnica montana* (Leopard's Bane), *Atropa belladonna* (Deadly Nightshade), *Bellis perennis* (Daisy), *Bryonia alba* (Wild Hops), *Cactus grandiflorus* (Night Blooming Cereus), *Caulophyllum thalictroides* (Blue Cohosh) *Cimicifuga racemosa* (Black Snakeroot), *Citrullus colocynthis* (Bitter Cucumber), *Cyclamen europaeum* (Sow-Bread), *Gelsemium sempervirens* (Yellow Jasmine), *Jonesia asoca* (The Asoka Tree), *Kali carbonicum* (Potassium Carbonate), *Lilium tigrinum* (Tiger Lily), *Rhamnus californica* (California Coffee Tree), *Juniperus sabina* (Savin), *Tilia europaea* (European Linden), *Viburnum opulus* (High Brush Cranberry), and any combination thereof.

The inactives portion may include a gel base. Various implementations of a gel base may include one, all, or any combination of the following: acrylates/C-10-30 alkyl acrylate cross-polymer, colloidal silver (preservative), potassium sorbate (preservative), citric acid (preservative), fulvic liquid minerals (which may be used in various implementations to amplify the homeopathic actives sub-atomic resonance), water, sodium hydroxide (neutralizer for polymers), and vegetable glycerin (USP, mild moisturizer). The fulvic liquid minerals used in various implementations may be any disclosed in Appendix A, which is hereby incorporated entirely herein by reference, and in various implementations, the base includes all of the 73 trace minerals listed in Appendix A. In various implementations, the water may be purified vortexed alkaline water. In a particular implementation, the gel base may include acrylates/C-10-30 alkyl acrylate cross-polymer, vegetable glycerin, colloidal silver, citric acid, fulvic liquid minerals, potassium sorbate, water, and sodium hydroxide.

In various implementations, the actives portion may be about 50%-90% by weight and the base may be about 10%-50% by weight. The potency of each one of the pluralities of active ingredients included in the actives portion may be between tincture to about 100×, between 1C to about 30C, or LM-1 to about LM-3.

Table 1 lists an implementation of the active ingredients which may be used in an actives portion:

TABLE 1

| Component | Dilution Range |
| --- | --- |
| *Apis mellifica* (Honey Bee) | Tincture (Tinct) - 100X, 1C-30C, LM-1 to LM-3 |
| *Arnica montana* (Leopard's Bane) | Tinct. - 100X, 1C-30C, LM-1 to LM-3 |
| *Atropa belladonna* (Deadly Nightshade) | Tinct. - 100X, 1C-30C, LM-1 to LM-3 |
| *Bellis perennis* (Daisy) | Tinct. - 100X, 1C-30C, LM-1 to LM-3 |
| *Bryonia alba* (Wild Hops) | Tinct. - 100X, 1C-30C, LM-1 to LM-3 |
| *Cactus grandiflorus* (Night Blooming Cereus) | Tinct. - 100X, 1C-30C, LM-1 to LM-3 |
| *Caulophyllum thalictroides* (Blue Cohosh) | Tinct. - 100X, 1C-30C, LM-1 to LM-3 |
| *Cimicifuga racemosa* (Black Snakeroot) | Tinct. - 100X, 1C-30C, LM-1 to LM-3 |
| *Citrullus colocynthis* (Bitter Cucumber) | Tinct. - 100X, 1C-30C, LM-1 to LM-3 |
| *Cyclamen europaeum* (Sow-Bread) | Tinct. - 100X, 1C-30C, LM-1 to LM-3 |
| *Gelsemium sempervirens* (Yellow Jasmine) | Tinct. - 100X, 1C-30C, LM-1 to LM-3 |
| *Jonesia asoca* (The Asoka Tree) | Tinct. - 100X, 1C-30C, LM-1 to LM-3 |
| *Kali carbonicum* (Potassium Carbonate) | Tinct. - 100X, 1C-30C, LM-1 to LM-3 |
| *Lilium tigrinum* (Tiger Lily) | Tinct. - 100X, 1C-30C, LM-1 to LM-3 |
| *Rhamnus californica* (California Coffee Tree) | Tinct. - 100X, 1C-30C, LM-1 to LM-3 |
| *Juniperus sabina* (Savin) | Tinct. - 100X, 1C-30C, LM-1 to LM-3 |
| *Tilia europaea* (European Linden) | Tinct. - 100X, 1C-30C, LM-1 to LM-3 |
| *Viburnum opulus* (High Brush Cranberry) | Tinct. - 100X, 1C-30C, LM-1 to LM-3 |

Another example of an implementation of a list of active ingredients in an actives portion may be found in the ingredient listing and dilutions in the product information listed in Appendix B, the disclosure of which is hereby incorporated entirely herein by reference. A wide variety of combinations of potential active ingredients at desired potencies are possible using the list of ingredients and dilutions disclosed in this document. The examples provided of each implementation are for the exemplary purposes of this disclosure. Those of ordinary skill in the art will readily be able to create additional implementations using the principles disclosed herein.

In various implementations, the base portion may be about 10%-50% of the total weight of the topical gel. The acrylates/C-10-30 alkyl acrylate cross-polymer (the International Nomenclature Cosmetic Ingredient (INCI) name) is a polymer gel designed to contain extremely low levels of benzene-containing residual solvent, in the range of 0.5 ppm. Such a polymer gel may exhibit rapid wetting properties not requiring agitation, high thickening efficiency, limited electrolyte tolerance, excellent clarity in applications, and superior aesthetic performance, depending upon the implementation selected. Implementations of such a polymer gel are marketed under the trade name CARBOPOL® Ultrez 10 NF Polymer by Lubrizol Advanced Materials of Cleveland, Ohio. Many conventional polymer gels are specified to contain 1000 ppm of residual benzene, which while within the limits set by the current edition of the United States Pharmacopoeia/National Formulary (USP/NF) for topical use, has been judged to be too high in many European countries, where the use of these polymer gels have been banned.

The use of sodium hydroxide (which may be in an 18% solution by weight) as a neutralizing agent to buffer the gel base to enable thickening of the polymer gel is in contrast with many conventional gels which utilize triethanolamine, which contains amines which are subjects of concern in the alternative health care industry in the U.S. and Europe. Colloidal silver solution is utilized as an anti-microbial agent in the base in various implementations. Because of the very small size of the particles of silver contained in this particular implementation of a structured silver solution, toxicity issues related to the use of other conventional colloidal silver products may be avoided. The use of the structured silver is in contrast with conventional gels, which utilize methylparaben and other parabens to act as preservatives and anti-microbial agents.

In particular implementations, the purified water utilized in implementations of the base may be vortexed to produce structured alkaline water.

In various implementations, the fulvic liquid minerals included in implementations of bases disclosed in this document may be any of various compositions extracted from fulvic mineral bases. In particular implementations, the fulvic liquid mineral composition may include 73 trace minerals (which may be the 73 trace minerals listed in Appendix A) extracted using a supplier's proprietary process that performs the extraction from a fulvic acid containing mineral base resulting in a liquid that is slightly alkaline rather than acidic. Without being bound by any theory, the inclusion of the fulvic liquid minerals will further potentiate the activity of the various homeopathic preparations included as active ingredients in the actives portion, although the fulvic liquid minerals are listed in the inactives portion. As previously discussed, the minerals may be any disclosed in Appendix A previously incorporated by reference. In implementations of the base/inactives portion, the fulvic liquid minerals may be diluted through a reverse osmosis restructured water filter as part of the process of preparation.

While the use of specific inactive ingredients is described above and in other descriptions of base/inactives implementations disclosed in this document, these disclosures are for the exemplary purposes of this disclosure only. Accordingly, base/inactives implementations that may be utilized may include, one, all, or any of the various inactive ingredients disclosed in this document in any desired ratio in order to produce, by non-limiting example, a desired viscosity, a desired dry time on the skin, a desired taste, a desired shelf life, a desired biological activity, a desired potentiation of the homeopathic activity of the active ingredients, or any other desired characteristic or property of a gel homeopathic preparation. In particular implementations, ethanol may be added to the base of topical gel implementations in weight percentages between about 0.2% to about 10% to aid in enhancing the drying of the gel on the surface of the skin after application and/or to achieve a desired viscosity of the gel at the time of application. A wide variety of base/inactives implementations may be constructed using the principles disclosed in this document.

To prepare the topical homeopathic preparation, the actives portion and the base portion may be blended together, with about 50%-90% of the weight of the final preparation coming from the actives portion and about 10%-90% of the weight of the final preparation coming from the inactive ingredients in the base in particular implementations.

In various implementations, the mixed composition may be packaged in an airless pump bottle configured to aid in dispensing by those suffering from limited dexterity and/or painful mobility. The pump bottle may have a volume of 15 ml in particular implementations and hold up to 16 grams of material. Such airless pump bottles may be designed to be incapable of aspirating the gel back into the tube because of an internal piston which, when depressed, is configured to eliminate the likelihood of the introduction of any contamination into the preparation. The blending and packaging processes may be performed in a FDA approved facility with a current Good Manufacturing Practices (cGMP) rating.

The topical gel preparation may be used by adults. To use, the subject may gently apply a thin layer of the gel sufficient to cover the entire affected area, specifically the lower abdomen and lower back if necessary. This application may take place immediately at the onset of menstrual cramping/pain from the ovaries. While various treatment method implementations may have the patient use as needed, in other implementations, the dosing may be limited to no more than 6 applications to the skin daily.

In places where the description above refers to particular implementations of homeopathic formulations and implementing components, sub-components, methods and sub-methods, it should be readily apparent that a number of modifications may be made without departing from the spirit thereof and that these implementations, implementing components, sub-components, methods and sub-methods may be applied to other homeopathic formulations.

What is claimed is:

1. A topical homeopathic formulation comprising:
an active portion comprising a plurality of active ingredients and a base comprising a plurality of inactive ingredients;
wherein the plurality of active ingredients comprise:
one of tinctures and homeopathic preparations of *Apis mellifica, Arnica montana, Atropa belladonna, Bellis perennis, Bryonia alba, Cactus grandifloras, Caulophyllum thalictroides, Cimicifuga racemosa, Citrullus colocynthis, Cyclamen europaeum, Gelsemium Sempervirens, Jonesia asoca, Juniperus Sabina, Kali carbonicum, Lilium tigrinum, Rhamnus californica, Tilia europaea, Viburnum opulus*, and any combination thereof; and
wherein the base comprises:
acrylates/C-10-30 alkyl acrylate cross-polymer.

2. The formulation of claim 1, wherein the base further comprises colloidal silver, potassium sorbate, citric acid, fulvic acid, water, sodium hydroxide, vegetable glycerin, and any combination thereof.

3. The formulation of claim 1, wherein the base is a gel base and comprises acrylates/C-10-30 alkyl acrylate cross-polymer, vegetable glycerin, colloidal silver, citric acid, fulvic liquid minerals, potassium sorbate, water, and sodium hydroxide.

4. The formulation of claim 3, wherein the fulvic liquid minerals comprises 73 trace minerals.

5. The formulations of claim 1, wherein the actives portion comprises 50% to 90% by weight of the total formulation and the inactives portion comprises 10%-50% by weight of the total formulation.

6. The formulations of claim 1, wherein the base comprises an 18% sodium hydroxide solution.

7. The formulations of claim 1, wherein the base comprises ethanol.

8. A topical homeopathic formulation comprising an active portion comprising a plurality of active ingredients and a base comprising a plurality of inactive ingredients, wherein the plurality of active ingredients comprise:
one of tinctures and homeopathic preparations of *Apis mellifica, Arnica montana, Atropa belladonna, Bellis perennis, Bryonia alba, Cactus grandifloras, Caulophyllum thalictroides, Cimicifuga racemosa, Citrullus*

*colocynthis, Cyclamen europaeum, Gelsemium Sempervirens, Jonesia asoca, Juniperus Sabina, Kali carbonicum, Lilium tigrinum, Rhamnus californica, Tilia europaea, Viburnum opulus*, and any combination thereof; and wherein the base comprises one of:

acrylates/C-10-30 alkyl acrylate cross-polymer and sodium hydroxide.

9. The formulation of claim 8, wherein the base further comprises one of:

colloidal silver, potassium sorbate, citric acid, fulvic acid, water, and vegetable glycerin.

10. The formulation of claim 8, further comprising fulvic liquid minerals comprising 73 trace minerals.

11. The formulation of claim 8, wherein the actives portion comprises 50% to 90% by weight of the total formulation and the inactives portion comprises 10%-50% by weight of the total formulation.

12. The formulation of claim 8, further comprising an 18% sodium hydroxide solution.

13. The formulation of claim 8, wherein the base comprises ethanol.

14. A topical homeopathic formulation comprising an active portion comprising a plurality of active ingredients and a base comprising a plurality of inactive ingredients, wherein the plurality of active ingredients comprise:

one of tinctures and homeopathic preparations of *Apis mellifica, Arnica montana, Atropa belladonna, Bellis perennis, Bryonia alba, Cactus grandifloras, Caulophyllum thalictroides, Cimicifuga racemosa, Citrullus colocynthis, Cyclamen europaeum, Gelsemium Sempervirens, Jonesia asoca, Juniperus Sabina, Kali carbonicum, Lilium tigrinum, Rhamnus californica, Tilia europaea, Viburnum opulus*, and any combination thereof; and wherein the base comprises acrylates/C-10-30 alkyl acrylate cross-polymer, vegetable glycerin, colloidal silver, citric acid, fulvic liquid minerals, potassium sorbate, water, and sodium hydroxide.

15. The formulation of claim 14, wherein the fulvic liquid minerals comprise 73 trace minerals.

16. The formulation of claim 14, wherein the actives portion comprises 50% to 90% by weight of the total formulation and the inactives portion comprises 10%-50% by weight of the total formulation.

17. The formulation of claim 14, further comprising an 18% sodium hydroxide solution.

18. The formulation of claim 14, wherein the base comprises ethanol.

* * * * *